US006218190B1

(12) United States Patent
Shine et al.

(10) Patent No.: US 6,218,190 B1
(45) Date of Patent: Apr. 17, 2001

(54) METHOD FOR TESTING A CELL SUSPENSION

(76) Inventors: Thomas Adam Shine, 220 Lawrence St., No. 3, Newhaven, CT (US) 06511; Ian Basil Shine, 444 Central Park West, New York, NY (US) 10025

( * ) Notice: Subject to any disclaimer, the term of this patent is extended or adjusted under 35 U.S.C. 154(b) by 0 days.

(21) Appl. No.: 09/101,039

(22) PCT Filed: Dec. 27, 1996

(86) PCT No.: PCT/GB96/03259

§ 371 Date: Aug. 4, 1998

§ 102(e) Date: Aug. 4, 1998

(87) PCT Pub. No.: WO97/24599

PCT Pub. Date: Jul. 10, 1997

(30) Foreign Application Priority Data

Dec. 29, 1995 (GB) .................................................. 9526676

(51) Int. Cl.$^7$ .................................................. G01N 33/48
(52) U.S. Cl. .................................. 436/63; 436/8; 436/18; 436/174; 436/179; 435/2; 435/372
(58) Field of Search .................................. 436/8, 10, 16, 436/18, 63, 174, 179; 435/2, 372; 702/21

(56) References Cited

U.S. PATENT DOCUMENTS

| 3,962,125 | | 6/1976 | Armstrong | 436/18 |
|---|---|---|---|---|
| 4,185,964 | * | 1/1980 | Lancaster | 436/17 |
| 4,213,876 | * | 7/1980 | Crews et al. | 436/18 |
| 4,278,936 | * | 7/1981 | Shine | 324/71.1 |
| 4,299,726 | * | 11/1981 | Crews et al. | 436/10 |
| 4,322,313 | * | 3/1982 | Raaijmakers | 436/2 |
| 4,346,018 | * | 8/1982 | Carter et al. | 436/17 |
| 4,358,436 | | 11/1982 | Graham | 435/7.25 |
| 4,506,018 | * | 3/1985 | North, Jr. | 436/10 |
| 4,535,284 | | 8/1985 | Groves et al. | 324/71.1 |
| 4,968,629 | * | 11/1990 | Lapicola | 436/18 |
| 5,008,202 | * | 4/1991 | Edmondson et al. | 436/18 |
| 5,125,264 | | 6/1992 | Beuzard | 73/61.75 |
| 5,227,304 | * | 7/1993 | Wong | 436/17 |

FOREIGN PATENT DOCUMENTS 0 115 077   8/1984   (EP) .

\* cited by examiner

Primary Examiner—Maureen M. Wallenhorst
(74) Attorney, Agent, or Firm—Burns, Doane, Swecker & Mathis, L.L.P.

(57) ABSTRACT

A method for testing a cell suspension comprises the steps of: (1) diluting a portion of the cell suspension such that the liquid of the diluted suspension has the same osmolality as the extra cellular liquid of the cell suspension (plasma), and (2) subjecting the cells in the diluted suspension formed in step (1) to a cell size measurement while suspended in said diluted suspension. The method involves the testing of cells at their in vivo osmolality, thereby minimizing the possibility of swelling over time and mimicking the cells in vivo condition in respect of its osmotic environment.

16 Claims, 2 Drawing Sheets

METHOD FOR TESTING A CELL SUSPENSION

TECHNICAL FIELD

The present invention relates to a method in which a sample of cell suspension is analysed to determine a parameter of the cells relating to size, for instance volume, diameter or shape. In the method the cells are tested after dilution and the size measurement is corrected to the environmental conditions, especially osmolality, of the sample as supplied.

BACKGROUND ART

The automated testing of blood samples has become an important part of many medical investigations. Automated instruments' speed and ease of use has made them a preferred method of producing a complete blood count (CBC) in hospital laboratories. As well as producing values of the number of cells in a sample, the apparatus is used to measure the average size of the cells.

Electronic particle counters typically use a sensor which detects particles in a restricted flow, producing a measure of particle size and count for each particular type of particle. The sensor usually detects a change in an electrical field, an alteration in the light scatter from a laser, a change in the magnetic field density or magnetic flux, or changes in the optical, acoustic or other physical properties of the cells or cell suspension and/or suspending liquid. Whatever type of sensor is used, it produces a signal which is a product of a particle's size, shape, trajectory, number and other properties, some of which may be measured concomitantly. Electronic particle counters which use a direct or alternating current as a method to detect particles can be referred to as electronic particle sizing devices (hereinafter referred to as EPS), and produce a characteristic change in voltage or current, usually recorded as a voltage pulse as a particle passes through a restriction (aperture).

Electronic particle sizing relies on two electrodes suspended in a conducting solution which are isolated from each other except for a single conducting channel which is traversed by cells or other small particles in suspension. As a particle passes through the channel (aperture) the physical characteristics of the channel temporarily alters in proportion to the particle's size. By measuring the properties of these changes, the size and concentration of particles is determined. This is performed on red cells, white cells and platelets and any free cell suspension and may be combined with stains or other techniques to further is differentiate the cells by any means (i.e. optically, NMR etc).

Commercial EPS instruments do not use an isotonic diluent to produce a cell suspension, but instead use a hypertonic diluent typically phosphate buffered saline (PBS) fixed at 30 to 50 mOsm/Kg above the population's mean plasma osmolality. It is well known that there is a natural range of plasma osmolalities amongst individuals. It is also well known that for all permeable cells with non-rigid walls, cell size varies with the osmolality of the buffer in which it is suspended. When performing an automated cell test, such as a CBC, manufacturers test cells in a single fixed hypertonic osmolality that has no known relationship to the osmolality of the plasma of the patient being tested. This causes errors in the size estimates produced because cells tend to swell upon standing in hypotonic buffers and shrink in hypertonic buffers and because the amount the cell swells in any buffer is patient specific. Manufacturers reduce this source of error by using hypertonic buffers which induce the least change in cell size over time (ie aging before testing) at the cost of accuracy and usually results in smaller cell size.

The method of the invention overcomes the above problems by testing cells at their in vivo osmolality, thereby minimizing the possibility of swelling over time and mimicking the cell's in vivo condition in respect of its osmotic environment. The most accurate in vitro measures of in vivo cell size is possible if cells are tested in a buffer of the same osmolality as their plasma, as this removes the need for "correction factors" to adjust for incorrect buffer osmolality. In existing technology these correction factors are always fixed because the individual's plasma osmolality is unknown or is not used in existing tests. Since it is reported that patients sometimes have a plasma osmolality 50 to 100 mOsm/Kg below the population mean and since manufacturers use buffers up to 50 mOsm/Kg above the mean, gross errors are sometimes induced. Although these large deviations are uncommon, they tend to occur in patient with severe illness in whom errors can easily have serious consequences. The present method circumvents this problem in two ways; either by measuring the patient's plasma osmolality and adjusting the buffer osmolality to match, or by testing the cells in their own plasma.

It is known that cells, especially blood cells, act as osmotic devices. Reducing the osmolality of the solution surrounding a red blood cell below a critical level will cause that cell first to swell, then become spherical, and form a ghost cell which slowly loses its contents, almost entirely haemoglobin, into the surrounding medium. This process, called haemolysis, can be induced osmotically using water, or by detergents (eg soap), venoms or other chemical, thermal, mechanical or electrical agents.

It is known that the critical osmolality at which haemolysis occurs can be determined by subjecting aliquots of a red blood cell suspension to a concentration gradient which may include stepped or continuous changes in concentration, for instance as described in DE-A-3103792.

It has been recognised that the osmolality of the plasma may vary from individual to individual and, occasionally, within an individual over time. When a sample of blood of an individual having plasma with abnormal osmolality is subjecting to particle sizing, the value which is obtained for the cell size when diluted in isotonic saline will be different to the in vivo cell size. The present invention seeks to correct such errors.

DISCLOSURE OF INVENTION

In a new method according to a first aspect of the invention a cell suspension is subjected to the following steps:

1) a portion of the cell suspension is diluted with a diluent which has the same osmolality as the extracellular liquid of the cell suspension (plasma), and
2) the cells in the diluted suspension formed in step 1 are subjected to a cell size measurement while suspended in the said diluted suspension.

In this aspect of the invention the diluent used in step 1 may be constituted by plasma separated from the starting cell suspension.3 Separation may, for instance, be carried out manually or by other means. In this case it is unnecessary to determine the osmolality of the plasma to produce an accurate osmotically correct cell size. It may, however, be preferred in addition for a reference measurement of cell size to be conducted using, in place of the plasma, a diluent of known composition having an osmolality equal to that of the plasma, which requires a determination of that osmolality. Alternatively the reference measurement of size may consist of a series of measurements in varying osmolality diluents as described below in step 5. This allows a determination of the size measurement by interpolation. These reference tests allow confirmation to be obtained that the plasma used as diluent in step 1 is not having an effect on the values obtained in the measurement step 2. If the values are different further investigations have to be made.

Alternatively for step 1 the osmolality of the starting cell suspension is determined and a diluent is then made up to that osmolality. The diluent may be made up using appropriate buffers of known concentrations in suitable amounts (eg using suitable amounts of hypotonic and hypertonic fluids). The osmolality is determined, for instance, by measuring the osmolality of the plasma of the starting cell suspension, usually after separating a portion of the cell suspension into cells and plasma. The osmolality can alternatively be calculated using standard blood chemistry analysis which measures the concentration of most of the molecules in the plasma which contribute to osmotic pressure or by using standard osmometers.

The value obtained from the cell size measurement carried out in step 2 can be used to determine the osmolality of the plasma, in a preferred embodiment of this aspect of the invention. In this embodiment the method further includes the following steps:

3) a further portion of the cell suspension is diluted in an aqueous diluent of known osmolality,
4) the cell size of the cells in the known osmolality diluent is measured,
5) the function of cell size change with changing osmolality from hypertonic to hypotonic for the cells of the cell suspension is determined, and
6) the function determined in step 5, the cell sizes determined in steps 2 and 4 and the osmolality of the diluent used in step 3 are used to calculate the osmolality of the plasma used in step 1.

In a variation of this method, instead of or in addition to using neat plasma in step 1, plasma diluted by a known amount (for instance 1 volume (per volume) or more, usually up to 20 volumes, for instance 2–10 volumes) of a diluent having known osmolality is used as diluent for the cells. Where this step is used in addition to step 1 using neat plasma this serves as a check on the cell size measurement determined in step 2 and hence on the value determined for the plasma osmolality calculated in step 6 above.

In this method the function determined in step 5 may be determined by several techniques. In one of these the cells of the cell suspension itself may be used to determine the function. In this method the following steps at least are carried out:

7) a portion of the starting cell suspension is diluted in an aqueous diluent of known hypertonic (with respect to the plasma of the starting cell suspension) osmolality to form a hypertonic diluted suspension.
8) the cell size of the cells in the hypertonic diluted suspension is measured,
9) a further portion of the cell suspension is diluted in an aqueous diluent of known osmolality (hypotonic with respect to the osmolality of the plasma of the starting cell suspension) to form a hypotonic diluted suspension,
10) the cell size of the cells in the hypotonic diluted suspension is measured, and
11) the cell size measurements obtained for the hypertonic and hypotonic diluted cell suspensions in steps 8 and 10 and the values of osmolality of the hypertonic and hypotonic diluent are used, to calculate the said function.

Since the function may not be linear within the range of osmolalities between the hypertonic and hypotonic diluent, it is preferred for the cell size measurements to be carried out for the diluted suspensions at several different known osmolalities in the range. Preferably the range includes a hypotonic osmolality at which the cells have their maximum size before bursting.

In another technique for determining the function in step 5 a calibrating cell suspension of a similar type to that of the starting cell suspension, but which has a well characterised shape change with changing osmolality is used to determine the function. The calibrating cell suspension is diluted using hypotonic and hypertonic diluents of various known concentrations and subjected to size measurements. This method is described further in our copending International patent applications, filed even date herewith, respectively claiming priority from British patent application Nos. 9526649.0, 9526684.7 and 9526720.9. To confirm that the function thereby determined is likely to be applicable to cells of the starting suspension the test can be carried out on several comparison cell suspensions of a similar type and the average of the population used as the function.

Having ascertained the function for the standard/comparison cells, it may be preferable for cell size measurements to be carried out on the cells of the starting cell suspension when diluted to at least two known osmolalities. Preferably at least one of these is a hypotonic osmolality at which the cells are at their maximum size without bursting, since this optimises the determination of the relevant constants for the cells of the cell suspension. It may be convenient for the cell size measurement to be carried out on several aliquots of cell suspension subjected to successively lower osmolality diluent including that at which the cells have their maximum size.

The method used in these embodiments of the invention for determining the osmolality of the plasma of the starting cell suspension used in step 1, may alternatively be used to determine the osmolality of any diluent of unknown osmolality. For instance, where a diluent is used to dilute a portion of starting cell suspension which is made up of a known proportion of plasma and a known proportion of diluent of known osmolality, the method can by used to determine the osmolality of the plasma. By this technique smaller quantities of plasma need be used as diluent which reduces the size of the sample of starting cell suspension required to provide the plasma. The method can, in effect, be used as an osmometer for use in the determination of osmolality of a variety of aqueous liquids, provided that the cells' response to a buffer of known osmolality is also determined.

In another method for determining the osmolality of the extracellular medium, it is used, either as such or after diluting with a known amount of a diluent of known, preferably about isotonic, osmolality, as a diluent for a series of tests on C-negative red blood cells having previously determined the function of size change with changing osmolality for these cells or other equally non-reactive cells. In the latter case, therefore, a calibration curve has been set up, using the calibrating cells, of cell size measurement against osmolality. The cell size measurement of those cells (or rather of a separate aliquot of the calibrating cell sample) when suspended in a medium from the cell sample under test, allows a determination of the osmolality of the extracellular liquid. Accordingly it may be necessary to make only a single determination of cell size measurement at a single dilution of the O-negative cell, although it often improves the accuracy and may be just as convenient, when using automated apparatus capable of setting up the concentration gradient of changing osmolality, to determine the cell size measurement over a range of osmolalities down to the concentration at which the cells have their maximum size.

Where successive aliquots of a diluted suspension and of comparison cell suspension or of a calibrating cell suspension are subjected to successively lower osmolality environments a profile of cell size measurement is obtained.

The data collected in any of the above embodiments where cells are subjected to a range of diluent osmolalities may allow a profile of the average cell size measurement against dilution to be created, or for a frequency distribution of cell size measurement of individual cells or of a fixed number of cells. It is preferred for the data to be collected on a cell-by-cell basis and for the results to be reported as a frequency distribution of a population of individual cells, as described in our copending application No. 9526720.9. The profiles (frequency distribution) from the various series of tests can be compared with one another, in particular maxima of the profiles and the shapes of the curves, to allow an interpolation to determine the osmolality of the extracellular medium or of other diluent whose osmolality is to be determined.

This technique can be used to determine the osmolality of the medium to such an accuracy that the value can be quoted to the nearest 0.1 or even 0.01 of a milliosmole. This is more accurate than existing conventional osmometers which can report values to the nearest 1 or 2 milliosmoles. A conventional osmometer may be used in conjunction with the present method to estimate the osmolality of the medium before the range of tonicities for the measurements for step 5 is arranged.

In each aspect of the invention the starting cell suspension is diluted preferably in a double dilution before being subjected to the respective cell size measurement step. In the double dilution each step dilutes by at least 10 volumes of diluent, usually at least 30 volumes, often at least 50 volumes, for instance up to 500 or 1000 volumes. The total dilution is usually in the range 4000–25,000. Suitable levels of dilution are twice 100 volumes (i.e. a total of 10,000).

In the method of the invention the cell size measurement which is made on the cell suspensions provides data about at least one size parameter of the cells. Although other methods of determining the particle size of cells, such as methods which determine an alteration in the light scatter, or other changes in the optical or acoustic or other physical properties can be utilised the measurement is usually determined using electronic particle sizing techniques, preferably determining the change in electric field as the diluted suspension passes through a restriction. The signal from the sensor is affected primarily by particles' size and shape, whilst the trajectory and, usually, number are kept approximately constant, using apparatus described in our copending application No. 9526652.4 filed even date herewith. From the data collected, information about the cells' size and shape under in vivo conditions can be determined using the methods of calculation described in the above-mentioned copending applications.

In summary, the present invention provides three methods of determining the true in vivo cell size. They are:
1) Determine the osmolality of the plasma and perform an EPS measurement (or other cell size measurement) in sample specific buffer of the same osmolality. The plasma osmolality may be determined by
   a) measuring the plasma with an osmometer,
   b) measuring the osmolality of the whole blood sample, and if the osmometer is particle sensitive and if the number and approximate size of the particles (cells) is known, their effect on the osmolality measurement can be determined and thus the correct osmolality can be calculated,
   c) determine the osmolality from standard blood chemistry analysis which measures the concentration of most of the molecules which contribute to osmotic pressure,
   d) determine the osmolality using the technique in (2) below.
2) In a second method, the osmolality of the plasma does not have to be determined. An aliquot of the cell suspension is tested to generate an osmolality/cell size curve and a similar aliquot of the cell suspension is diluted in part or entirely by the patients own plasma and tested using standard sizing techniques (preferably using the same particle sizing device). When the size measurement from the second test is compared to the first test curve, in vivo plasma osmolality can be determined. From this determination, an osmolality-correct size measurement is realised, which may be further improved by using the technique described in our co-pending application No. 9526649.0 filed even date herewith.
2.b) The method described in the preceding paragraph may be modified by using the plasma when running an osmolality/cell size curve and a fixed diluent for a standard size measurement, or using diluted plasma instead of an whole plasma sample. Further, the entire curve need not be run, and only a portion of it, or even only a single different point on the curve may be sufficient to determine the correct size, provided that the function of the curve has been determined.
3) The osmolality-correct size may be completely determined from a single measure of the cells suspended in their own plasma.

BRIEF DESCRIPTION OF DRAWINGS

The accompanying figures show the results of the examples, specifically.

DETAILED DESCRIPTION

The invention is illustrated further in the accompanying examples:

EXAMPLE 1

Cell Suspension Under Test

A portion of a sample (sample volume 0.1 to 2 $\mu l$ upwards) of blood is diluted twice by 100 volumes (per volume of the portion of sample) of buffered saline at 290 mOsm/kg, but ranging form 200 to 400 mOsm/kg. Successive aliquots of the diluted suspension are then subjected to successively increasing amounts of a hypotonic diluent, which in this example is deionised water to subject the cells to osmolalities in the range 400 mOsm/kg to 0 mOsm/kg (or equivalent resistance of 2 kΩ to 18.3 MΩ). The further diluted suspensions then pass through the measuring chamber of an electronic particle size spectroscopy apparatus (as illustrated in our copending application No. 9526652.4 filed even date herewith. The flow rate is about 5000 cells per second through the aperture (representing about 10% of the suspension and hence of the cells). The remaining 90% of the suspension is drained to waste. (In alternative embodiments it may be desirable for all or substantially all the cells to be subjected to the cell size measurement and thus to pass through the aperture, for instance where the original sample size is extremely small.)

The electrical pulse for individual cells passing through the aperture is measured by an analogue peak detection circuit which measures the maximum voltage of each pulse detected. This allows the analogue pulse to be converted to digital data signals. The detector is serviced about ten times as often as a cell passes through the aperture, that is about $5 \times 10^4$ times per second. Each digital conversion of a cell's voltage is performed more quickly than a cell traverses the aperture. These data can be analysed and displayed in real time and/or stored for comparative analyses. Alternatively, the pulse may be continuously digitized using very high speed analogue to digital converters (<1μS conversion time) eliminating the need to peak detection by comparing the digitized values as a cell traverses the aperture.

Figure 1:
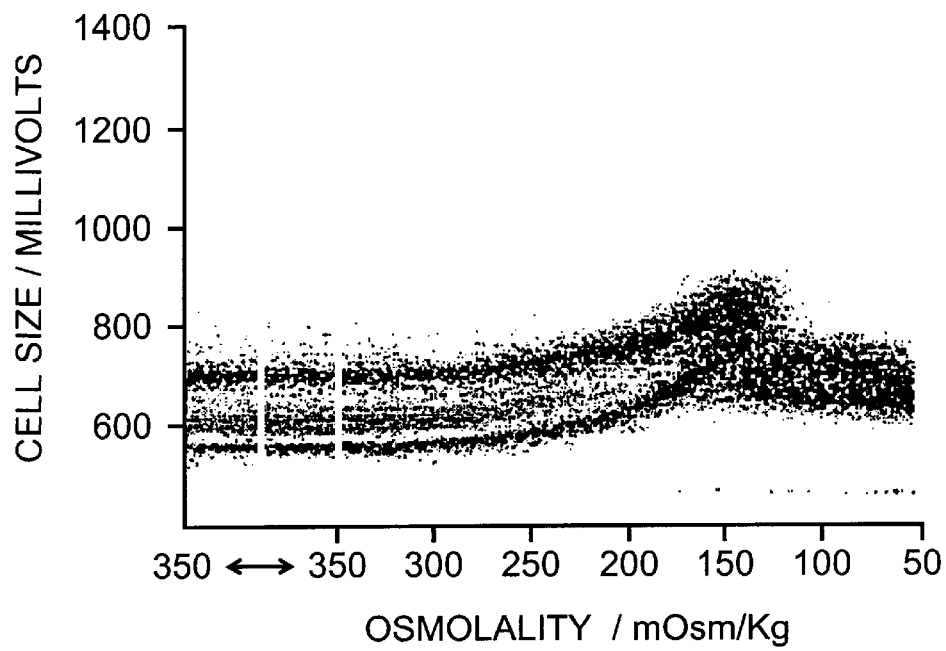
FIG. 1 shows a frequency distribution indicating the profile of the cell size measurement against osmolality for a sample of cells under test from hypertonic osmolality to an osmolality below that at which the cells burst.
Figure 2:
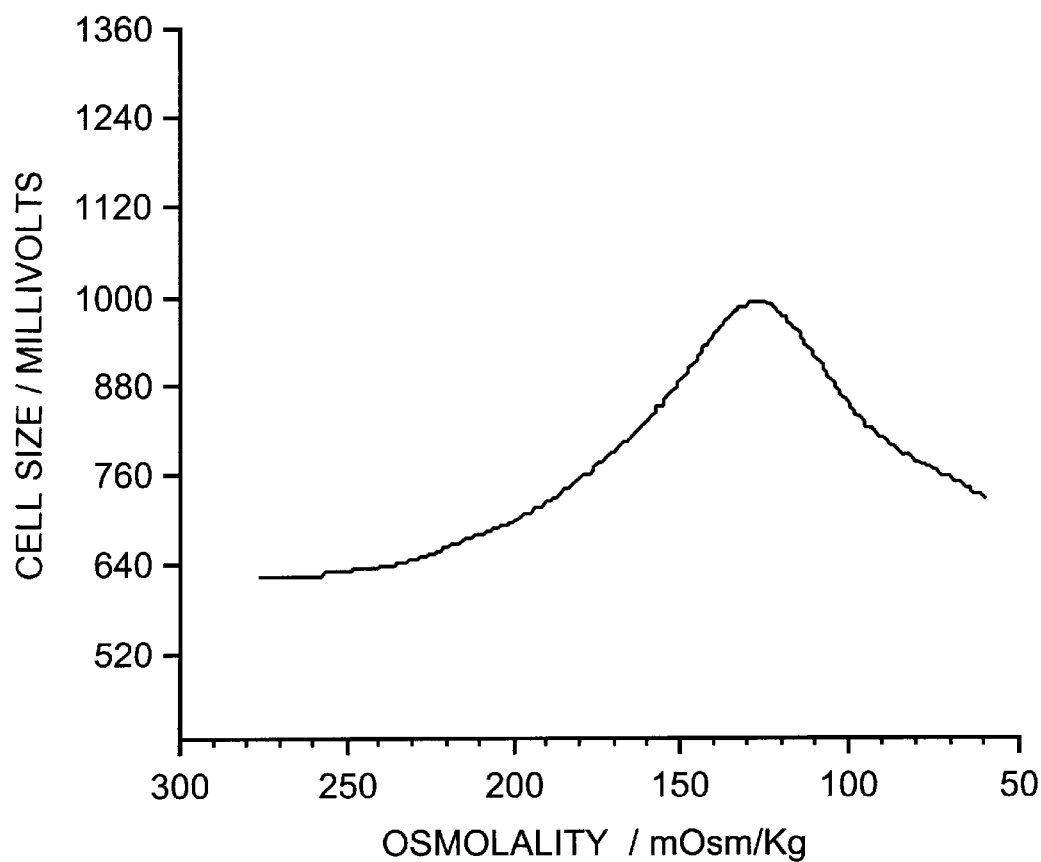
FIG. 2 shows that the mean cell size measurement derived from the results indicated in FIG. 1.

From these data a value for a cell size measurement parameter for each cell is determined. The frequency distribution for the values is plotted against osmolality of the suspending liquid, which is calculated from the quantities of buffered saline and of water for the aliquot under observation (or it may be measured during the test), for all osmolality values down to the value below which the cells react to reach their maximum size and burst. The frequency distribution is shown in FIG. 1. FIG. 2 shows the mean cell size value against osmolality for the data from FIG. 1.

The maximum of the curve is the point at which the cells are at their maximum cell size ($cm_{max}$). Above this dilution, or below the osiolality $O_b$, the cells burst. At isotonic osmolality the cells have cell size measurement $cm_i$.

If the extracellular medium of the original cell suspension under test has an osmolality greater than the buffer osmolality i.e. is hypertonic $O_y$, the true cell size measurement $cm_y$ of the cells in vivo will be lower than that determined at the plasma osmolality. Similarly if the extracellular medium of the original suspension is lower than average ($O_o$) the true in vivo cell size measurement ($cm_o$) will be higher than that determined at the plasma osmolality.

EXAMPLE 2

Calibration-Curve

Figure 3:
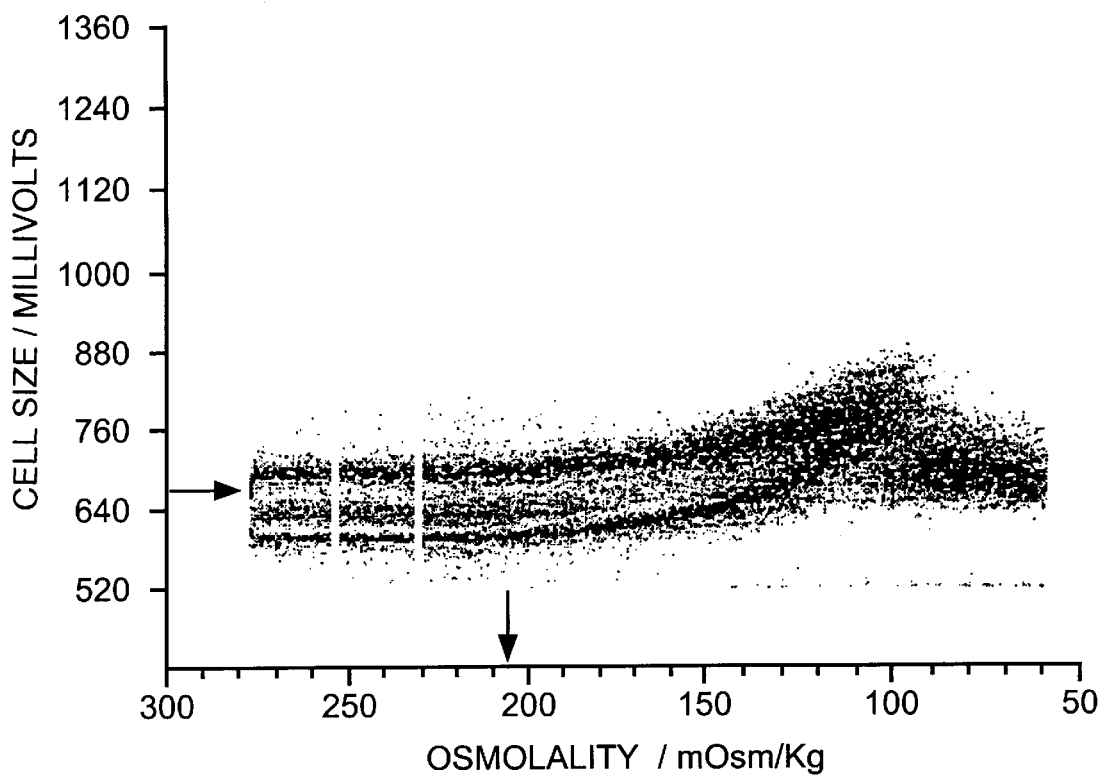
FIGS. 3 and 4 shows a calibrating curve which are the frequency distribution and the profile of the mean cell size measurement, respectively, of a sample of calibrating red blood cells against dilution from hypertonic to an osmolality below that at which the calibrating cells burst, and includes an indication of a determination of the cell size measurement of the calibrating cells suspended in medium including a known amount of extracellular medium of the sample of cells under test.

A sample of O-negative red blood cells is subjected to the same general method as the cells under test in example 1 to generate the frequency distribution profile shown in FIG. 3.

Figure 4:
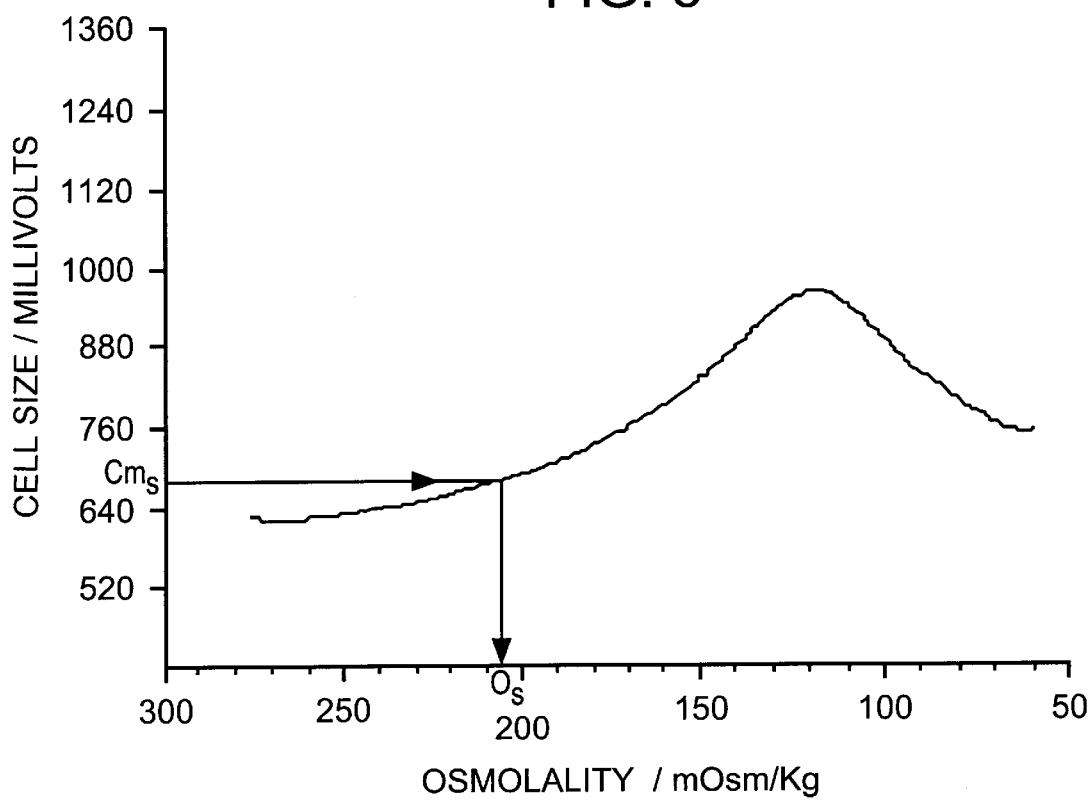

A second portion of the blood sample used in example 1 is separated by centrifugation to remove cells from the extracellular liquid. The extracellular liquid is then diluted with 9 volumes of buffered saline as used in example 1 to dilute the first portion of the cell sample. This medium was then used to dilute a portion of the calibrating O-negative red blood cells and the cell size measurement of those cells determined as $cm_s$. The value for the osmolality of the cells having that cell size measurement is determined as shown in FIG. 4 to be $O_s$. From this value the osmolality of the extracellular medium can be calculated. This value can then be used to determine the in vivo cell size measurement for the cells of the sample from the profile shown in FIGS. 3 and 4.

Similar results can be achieved if voltages values other than the peak voltage are measured, for instance if the height of each pulse is determined at several intervals and/or the area under the voltage/time curve is measured. The data is generally converted to digital where the data are collected on a cell-by-cell basis. It may be possible to measure the average cell size only, by using standard data collection techniques in which the voltages of a known number of cells are summated, although the accuracy of such techniques may not be good enough to obtain adequate results in the methods of the present invention.

What is claimed is:

1. A cell size measurement method for a cell suspension comprising cell and extracellular liquid plasma, the method comprising:
   1) determining the osmolality of the extracellular liquid plasma of the cell suspension;
   2) diluting a portion of the cell suspension with a diluent which has the determined osmolality to form a diluted suspension; and
   3) subjecting the cells in the diluted suspension formed in step 2 to a cell size measurement while suspended in the diluted suspension; wherein the osmolality of the extracellular liquid plasma in step 1 is determined by:
      i) diluting a portion of the cell suspension in at least one aqueous diluent of known osmolality;
      ii) measuring the cell size of the cells in the known osmolality diluent;
      iii) determining a function of cell size change based on changing osmolality from hypertonic to hypotonic for the cells of the cell suspension; and
      iv) using the function determined in step iii, the cell size determined in step ii and the osmolality of the diluent used in step i to calculate the osmolality of the plasma used in step 1.

2. A method according to claim 1 in which the function in step iii is determined by carrying out the following steps:
   a) diluting a portion of the starting cell suspension in an aqueous diluent of known hypertonic osnolality to form a hypertonic diluted suspension;
   b) measuring the cell size of the cells in the hypertonic diluted suspension;
   c) diluting a further portion of the cell suspension in an aqueous diluent of known hypotonic osmolality to form a hypotonic diluted suspension;
   d) measuring the cell size of the calls in the hypotonic diluted suspension; and
   e) using the cell size measurements obtained for the hypertonic and hypotonic diluted cell suspensions in steps b and d and the values of osmolality of the hypertonic and hypotonic diluent, to calculate said function.

3. A method according to claim 2 in which steps c and d are carried out with diluents of differing known hypotonic osmolalities and steps a and b are carried out with diluents of differing known hypertonic osmolalities.

4. A method according to claim 1 in which cell size measurements are conducted by dilating at least two further portions of the cell suspension with diluents of at least two known hypotonic osmolalities and subjecting the cells in each of the diluted suspensions to a cell size measurement.

5. A method according to claim 4 in which a maximum cell size is thereby determined.

6. A method according to claim 4 in which a maximum cell size has been predetermined and a calibration curve of cell size against osmolality generated from said cell size measurements in the presence of known osmolality diluents, is used to determine the osmolality of a diluent of unknown osmolality by diluting a further portion of the cell suspension with a known amount of said diluent of unknown osmolality and a known amount of a diluent of known osmolality, and measuring the cell size of the cells in the suspension thereby produced.

7. The method according to claim 4, in which the diluents comprise at least one diluent which has an osmolality such that the cells increase in size to their maximum cell size value or a lower osmolality.

8. A method according to claim 1 in which the cells are blood cells.

9. A cell size measurement method for a cell suspension comprising cells and extracellular liquid plasma, the method comprising:
   1) determining the osmolality of the extracellular liquid plasma of the cell suspension;
   2) diluting a portion of the cell suspension with a diluent which has the determined osmolality to form a diluted suspension; and
   3) subjecting the cells in the diluted suspension formed in step 2 to a cell size measurement while suspended in the diluted suspension; in which the diluent used in step 2 is constituted by plasma separated from the starting cell suspension.

10. A method for determining the osmolality of an aqueous liquid in which a known amount of the liquid is used, optionally in admixture with a known amount of a reference diluent of known osmolality, to dilute a portion of cells having a predetermined dependence of size change with change in osmolality of surrounding medium, which comprises the steps of subjecting the diluted portion of cells to a cell size measurement, and using the cell size measurement obtained to calculate the osmolality of the aqueous liquid.

11. A method according to claim 10 in which the aqueous liquid is plasma.

12. A method according to claim 10 in which the cells are O-negative blood cells.

13. A method according to claim 10 in which several portions of the cells are suspended in portions of increasing hypotonic osmolality reference diluent, each including a known amount of said aqueous liquid and a known amount of a hypotonic reference diluent of known hypotonic osmolality, and a cell size measurement is carried out for each diluted suspension and used to calculate the osmolality of the aqueous liquid.

14. The method according to claim 13, in which at least one of the diluted suspensions has an osmolality at or below that which causes the cells to increase in size to their maximum size.

15. A method in which a cell suspension comprising cells and extracellular liquid plasma is subjected to the following steps:
   1) a portion of the cell suspension is diluted with a diluent to form a diluted suspension, wherein said diluent is constituted by plasma separated from the starting cell suspension; and
   2) the cells in the diluted suspension formed in step 1 are subjected to a cell size measurement while suspended in said diluted suspension.

16. A method of determining the osmolality of a cell suspension comprising cells and extracellular liquid plasma, the method comprising:
   1) diluting the cell suspension using a diluent constituted by plasma separated from the starting cell suspension to form a diluted susenion;
   2) subjecting the cells in the diluted suspension formed in step 1 to a cell size measurement at a number of different concentrations;
   3) diluting a further portion of the cell suspension using a reference diluent of known osmolality to form a diluted suspension;
   4) subjecting the cells in the diluted suspension formed in step 3 to a cell size measurement at a number of different known concentations; and
   5) using the cell size measurements obtained in steps 2 and 4 and the known osmolality of the reference diluent in step 3 to calculate the osmolality of the extracellular liquid plasma of the cell suspension;
      wherein, in both steps 2 and 4, the cell suspension is diluted over a range of different concentrations such that the cells reach maximum cell size and the osmolality of the plasma is calculated from the change in concentration in each of steps 2 and 4 to reach maximum cell size and the known osmolality of the reference diluent.

* * * * *